United States Patent
Samproni (10) Patent No.: US 11,260,388 B2
(45) Date of Patent: Mar. 1, 2022

(54) SYSTEM INCLUDING A SENSOR ARRAY WITH SELECTIVE PARTITIONING

(71) Applicant: Siemens Healthcare Diagnostics Inc., Tarrytown, NY (US)

(72) Inventor: Jennifer Samproni, Braintree, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 304 days.

(21) Appl. No.: 16/468,944

(22) PCT Filed: Dec. 13, 2017

(86) PCT No.: PCT/US2017/066051
§ 371 (c)(1),
(2) Date: Jun. 12, 2019

(87) PCT Pub. No.: WO2018/112017
PCT Pub. Date: Jun. 21, 2018

(65) Prior Publication Data
US 2019/0336963 A1     Nov. 7, 2019

Related U.S. Application Data

(60) Provisional application No. 62/435,346, filed on Dec. 16, 2016.

(51) Int. Cl.
*B01L 3/00*     (2006.01)
*G01N 33/487*     (2006.01)

(52) U.S. Cl.
CPC ........ *B01L 3/502* (2013.01); *G01N 33/48707* (2013.01); *B01L 2300/024* (2013.01);
(Continued)

(58) Field of Classification Search
CPC ....... B01L 2300/024; B01L 2300/0645; B01L 2300/0663; B01L 2300/0832; B01L 3/502; G01N 27/3272; G01N 33/48707
See application file for complete search history.

(56) References Cited

U.S. PATENT DOCUMENTS

2002/0187560 A1* 12/2002 Pezzuto ................ B01F 5/0471
436/180
2006/0245978 A1    11/2006 Prins
(Continued)

FOREIGN PATENT DOCUMENTS

WO      2016011308 A1     1/2016

OTHER PUBLICATIONS

International Search Report and Written Opinion of International Application No. PCT/US2017/066051 dated Feb. 16, 2018.

*Primary Examiner* — Jennifer Wecker
*Assistant Examiner* — Jonathan Bortoli
(74) *Attorney, Agent, or Firm* — Dunlap Codding, P.C.

(57) ABSTRACT

A system that include an sample analyzer having a sensor array. The sensor array includes a housing having a base, a top spaced above the base, and an outer wall that extends from the base to the top. The sensor array includes an inlet that is sized to receive a sample of the fluid, and a plurality of partitions arranged around the fluid inlet. Each partition has a port at the fluid inlet for receiving a portion of the sample of fluid received by the fluid inlet. The sensor array includes at least one sensor in each partition. The sensor array is configured to selectively direct the sample of fluid received by the fluid inlet into one or more of the plurality of partitions into contact the at least one sensor.

20 Claims, 5 Drawing Sheets

(52) U.S. Cl.
CPC .......... *B01L 2300/0645* (2013.01); *B01L 2300/0663* (2013.01); *B01L 2300/0832* (2013.01)

(56) References Cited

U.S. PATENT DOCUMENTS

2012/0143531 A1* 6/2012 Davey .............. G01N 33/48785
702/51
2013/0139584 A1   6/2013 Qasimi et al.
2015/0082874 A1   3/2015 Samproni et al.

\* cited by examiner

SYSTEM INCLUDING A SENSOR ARRAY WITH SELECTIVE PARTITIONING

This application claims priority to U.S. Provisional Application No. 62/435,346, filed Dec. 16, 2016, the disclosure of which is hereby incorporated by reference in its entirety.

TECHNICAL FIELD

The present disclosure relates to a system having sensor array configured for selective partitioning of a sample of fluid.

BACKGROUND

Various types of tests related to patient diagnosis and therapy can be performed by analysis of a sample, such as a patient's bodily fluids, using automated sample analyzers. Such sample analyzers obtain measurements from the sample in order to determine the presence and/or amount of analyte of interest. In typical sample analyzers, as the number of analytes for detection increase the required sample volume increases. However, low sample volumes are desirable when the sample is limited, such as in the case of whole blood from neonatal patients, or when the sample itself is expensive. Although various known clinical analyzers for chemical, immunochemical and biological testing of samples are available, analytical clinical technology is challenged by increasing needs for improved levels of analysis while reducing sample volume requirements.

SUMMARY

An embodiment of the present disclosure is a sensor array. The sensor array includes a housing having a base, a top spaced above the base, and an outer wall that extends from the base to the top. The sensor array includes an inlet that is sized to receive a sample of the fluid and a plurality of partitions arranged around the fluid inlet. Each partition has a port at the fluid inlet for receiving a portion of the sample of fluid received by the fluid inlet. The sensor array includes at least one sensor in each partition. The sensor array is configured to selectively direct the sample of fluid received by the one or more of the plurality of partitions from the fluid inlet into contact with the at least one sensor.

Another embodiment of the present disclosure is a system that includes a sample analyzer. The sample analyzer may include a sensor array and at least one computing device. The sensor array includes a housing having a base, a top spaced above the base, and an outer wall that extends from the base to the top. The sensor array includes an inlet that is sized to receive a sample of the fluid and a plurality of partitions arranged around the fluid inlet. The sensor array includes at least one sensor in each partition. The computing device is configured to control the selective partitioning of the sample of fluid into the one or more of the plurality of partitions. The computing device is also configured to analyze the sample of fluid in response to receiving a response signal from the at least one sensor when the sample of fluid contacts the at least one sensor.

BRIEF DESCRIPTION OF THE DRAWINGS

The foregoing summary, as well as the following detailed description of illustrative embodiments of the present application, will be better understood when read in conjunction with the appended drawings. For the purposes of illustrating the present application, there is shown in the drawings illustrative embodiments of the disclosure. It should be understood, however, that the application is not limited to the precise arrangements and instrumentalities shown.

DETAILED DESCRIPTION OF ILLUSTRATIVE EMBODIMENTS

Figure 1:
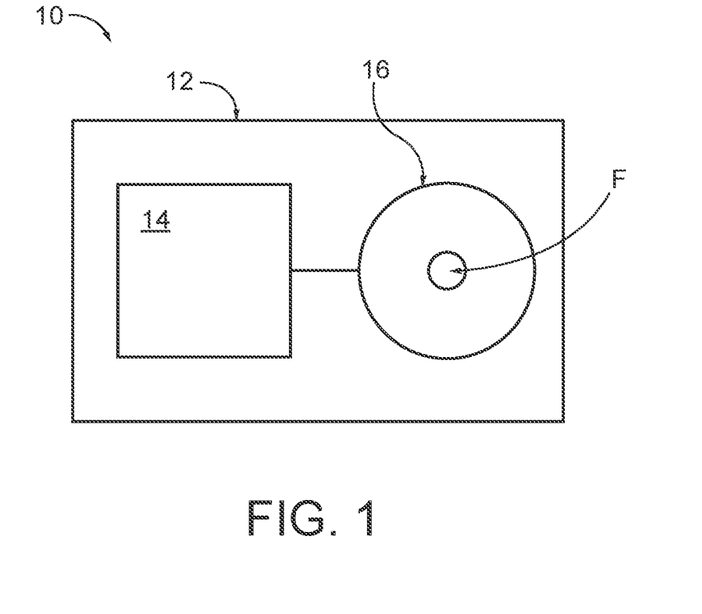
FIG. 1 is a schematic diagram of a sample analysis system with a partitioned sensor array according to an embodiment of the present disclosure.
Figure 2:
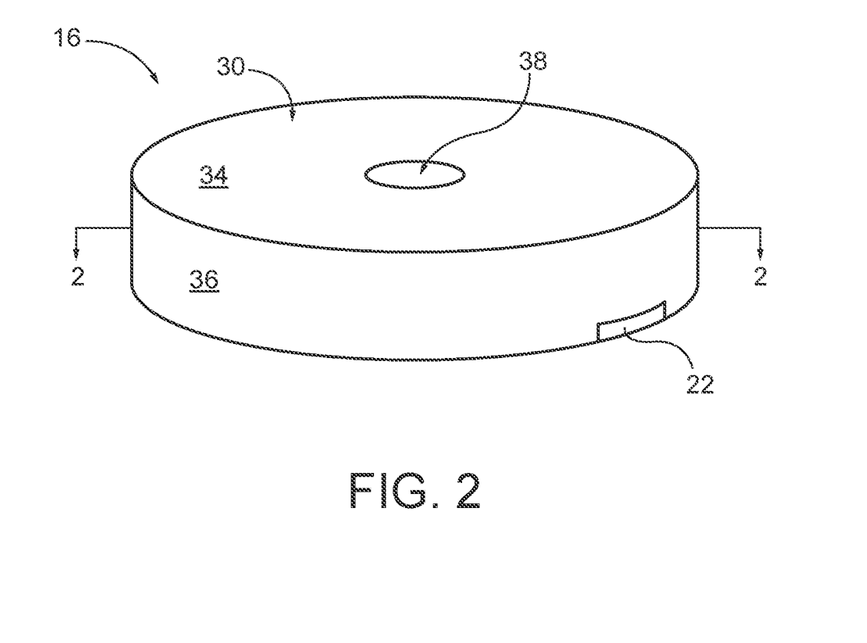
FIG. 2 is a perspective view of a sensor array illustrated in FIG. 1.

Turning to FIGS. 1 and 2, an embodiment of the present disclosure includes a test system 10 for analyzing a fluid F. The test system 10 includes a sample analyzer 12. The sample analyzer 12 has a computing device 14 and a sensor array 16 in electronic communication with the computing devices 14. The sensor array 16 includes one or more sensors 20 (FIG. 3) configured to detect analytes of interest in a sample of the fluid F. The sample analyzer 12 is configured to selectively partition the sample fluid F in order to direct the sample of fluid F into contact with different sensors 20 in the sensor array 16. The partitioning of the sample of fluid F allows the sample analyzer 12 to analyze the fluid for wide range of analytes using lower sample volumes. Conventional sample analyzers require higher sample volumes to in order to achieve similar breadth of analyte detection that is possible using the inventive concepts disclosed in the present application.

The sample analyzer 12 may be used to test any particular fluid F. For example, the fluid F may a biological fluid, such as whole blood, plasma, pleural fluids, urine, and/or dialysate fluids or other fluids obtained from a patient. Furthermore, the fluid F may also include non-biological sample liquids. The fluid F is not limited strictly to liquids obtained from a patient.

The computing device 14 includes electrical components that control operation of sample analyzer 12 and implement analytical techniques for analyzing data generated by the sensor array 16. The computing device 14 and its components provide an interface for the user to control operation of the sample analyzer 12. In one example, the computing device 14 has a processing portion (e.g. a computer processor and/or a controller), a memory portion, an input-output portion, a user interface, and one or more software applications. The software application executes instructions for controlling operation of the sample analyzer 12 and its components. The software applications also analyze data generated by the sensor array 16 as noted above. The computing device 14 may also be configured as a controller. In such an embodiment, the controller may include one or more processors, memory, and input/output links.

The sample analyzer 12 may include dispensing equipment (not shown) used to deliver sample of fluid F into sensor array 16. The dispensing equipment may include a motor that powers an arm controlled by the motor. The arm is adapted to deliver the sample of fluid F to the sensor array 16 via a pipe, tube, cartridge, insert, or other device for holding a sample. In another embodiment, the dispensing equipment can deliver sample of fluid F directly sensor array 16. In one example, the arm is moveable to deliver the sample of fluid F to the sensor array 16. Alternatively, the sensor array 16 is moveable relative to a fixed arm to receive the sample of fluid F. The computing device 14 may include a software application that when executed by the computer processor, controls operation of the dispensing equipment. The dispensing equipment could also be externally activated and/or externally controlled.

Figure 3:
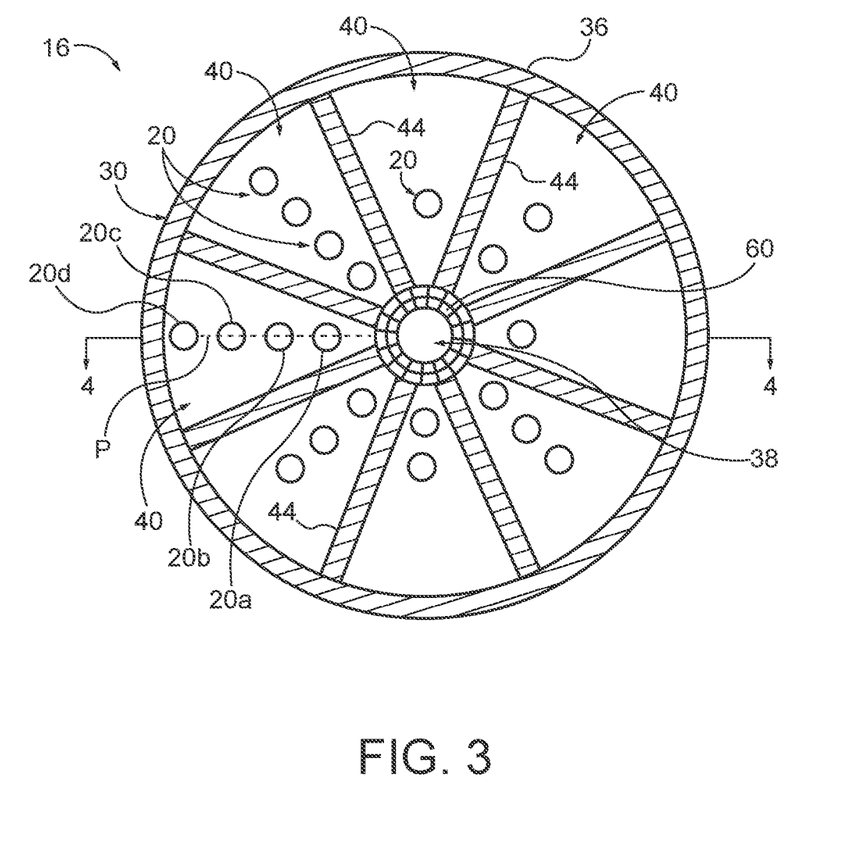
FIG. 3 is a top cross-sectional view of the sensor array taken in along line 3-3 in FIG. 2.
Figure 4:
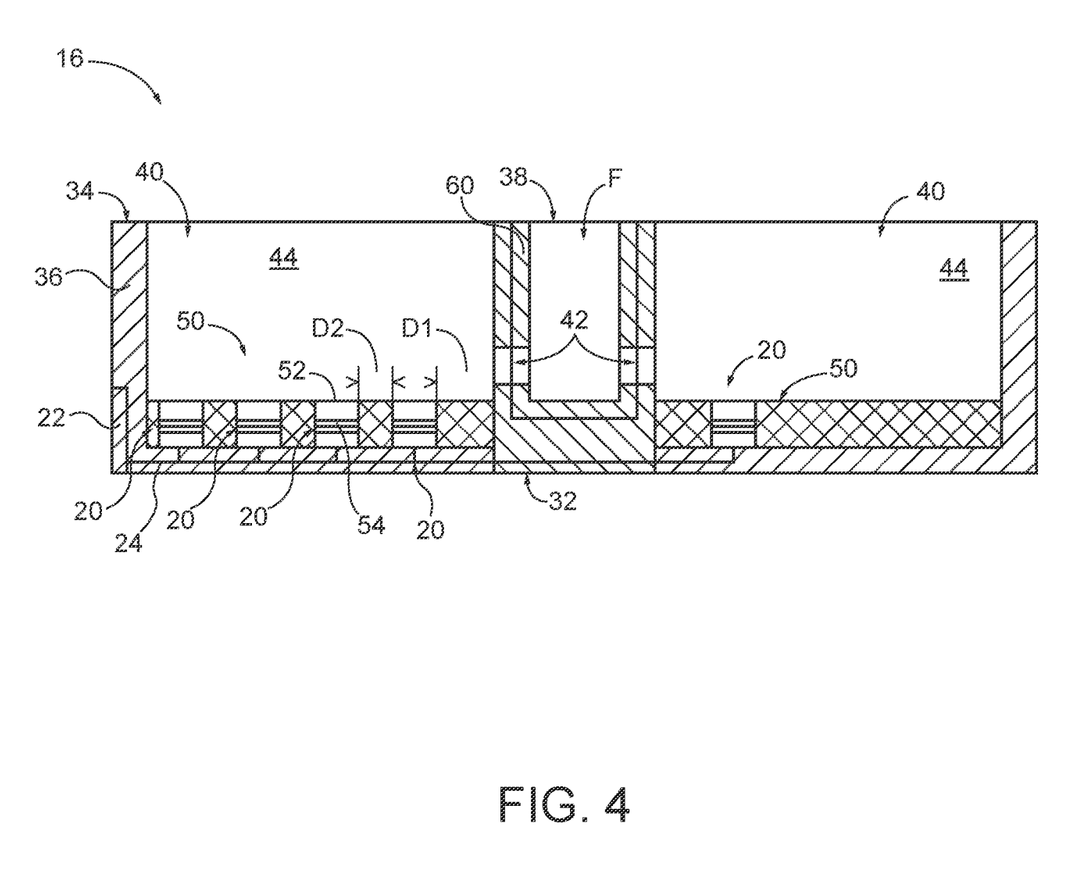
FIG. 4 is a cross-sectional view of a portion of the sensor array taken along line 4-4 in FIG. 3.

Continuing with FIGS. 2-4, the sensor array 16 includes a housing 30, a fluid inlet 38 configured to receive a sample of the fluid F and a plurality of partitions 40 arranged around the fluid inlet 38. One or more sensors 20 are located in each partition 40 as explained further below. The sensor array 16 also includes a fluid control device 60 that may be used to selectively direct the sample of fluid F from the fluid inlet 38 into the different partitions 40.

Continuing with FIGS. 2-4, the housing 30 has a base 32, a top 34 spaced above the base 32, and an outer wall 36 that extends from the base 32 to the top 34. The housing 30 also includes interior walls 44 that extend from the fluid inlet 38 to the outer wall 36. Adjacent pairs of interior walls 44 form different partitions 40 in the sensor array 16. The interior walls 44 isolate one partition from adjacent partitions so that the partitions 40 are substantially separate from each other. As illustrated, the plurality of partitions 40 extends radially outward from the fluid inlet 38 to the outer wall 36.

Figure 5:
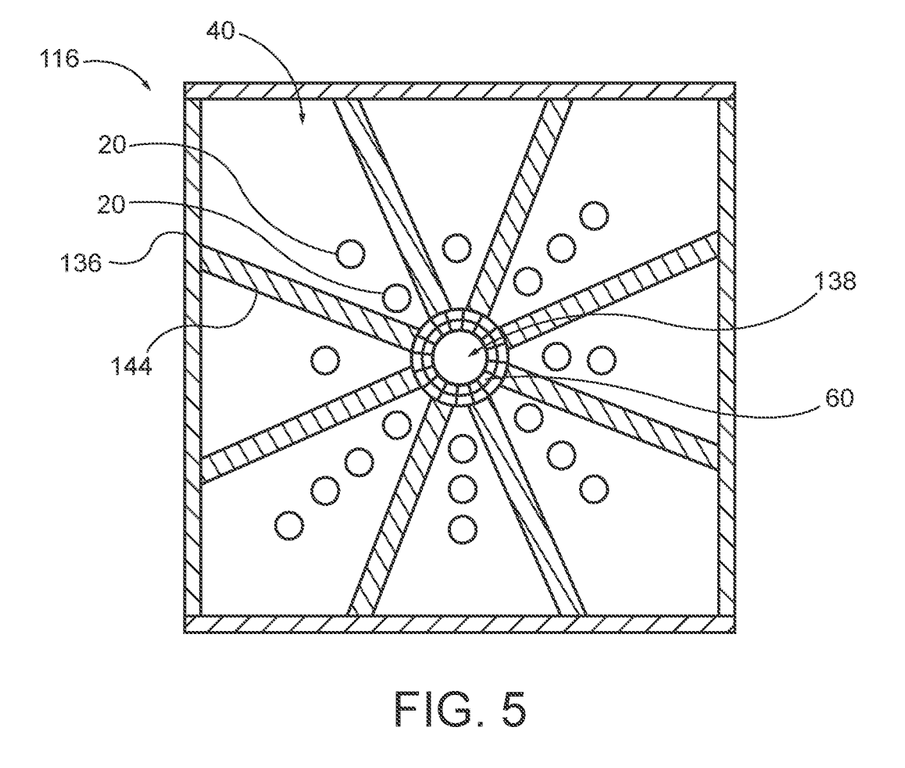
FIG. 5 is a top sectional view of the sensor array according to another embodiment of the disclosure.
Figure 6:
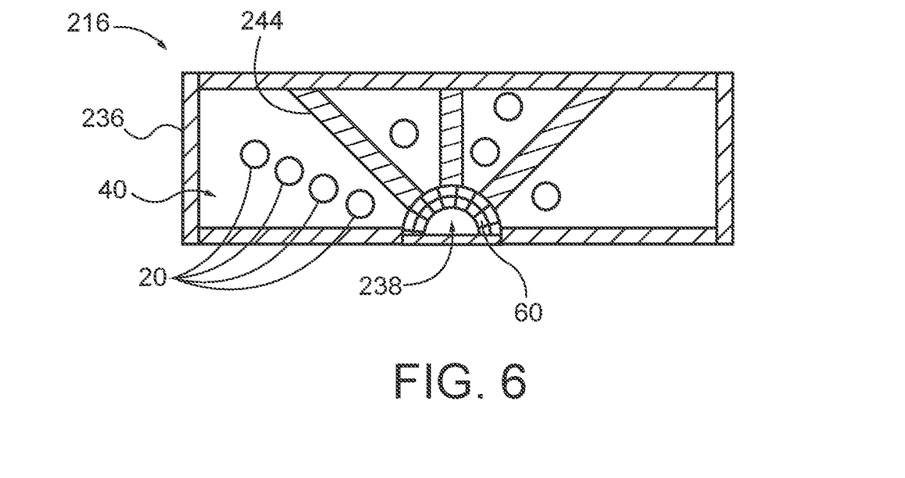
FIG. 6 is a top sectional view of the sensor array according to another embodiment of the disclosure.

The housing 30 can have a variety of cross-sectional shapes. As shown in FIGS. 1 to 4, the outer wall 36 has a substantially circular cross-sectional shape along a plane (not shown) that is parallel to the base 32. Alternatively, the outer wall 36 may have other cross-sectional shapes as shown in FIGS. 5 and 6. The sensor array 116 shown in FIG. 5 and the sensor array 216 shown in FIG. 6 are substantially similar to the sensor array 16 shown in FIGS. 2-4. Accordingly, the same reference numbers are used to identify features that are common between sensor array 16, sensor array 116, and sensor array 216. As shown in FIG. 5, the sensor array 116 has a rectilinear shaped outer wall 136 and interior walls 144 that extend from the fluid inlet 138 to the outer wall 136 to define the partitions 40. The fluid inlet 138 is positioned centrally with respect to the outer wall 136. In the embodiment shown in FIG. 6, the sensor array 214 has a fluid inlet 238 that is positioned adjacent to the outer wall 236. The interior walls 244 extend from the fluid inlet 238 to the outer wall 236 to define the different partitions 40.

Referring back to FIGS. 2-4, the sensor array 16 has a plurality of partitions 40. In accordance with the embodiment shown in FIGS. 2-4, the sensor array 16 has eight separate partitions 40. In alternative embodiments, the sensor array 16 has fewer than eight partitions. Accordingly, the present application is not limited to eight partitions shown in FIGS. 3 and 5. Rather, the sensor array 16 may include two partitions, three partitions, or four or more partitions 40. In still other embodiments, the sensor array 16 has more than eight partitions. The partitions 40 may have different sizes. For instance, in one example, the plurality of partitions includes a first partition having a first volume and a second partition having a second volume that is greater than the first volume. However, the partitions may be similarly sized as needed.

Figure 7:
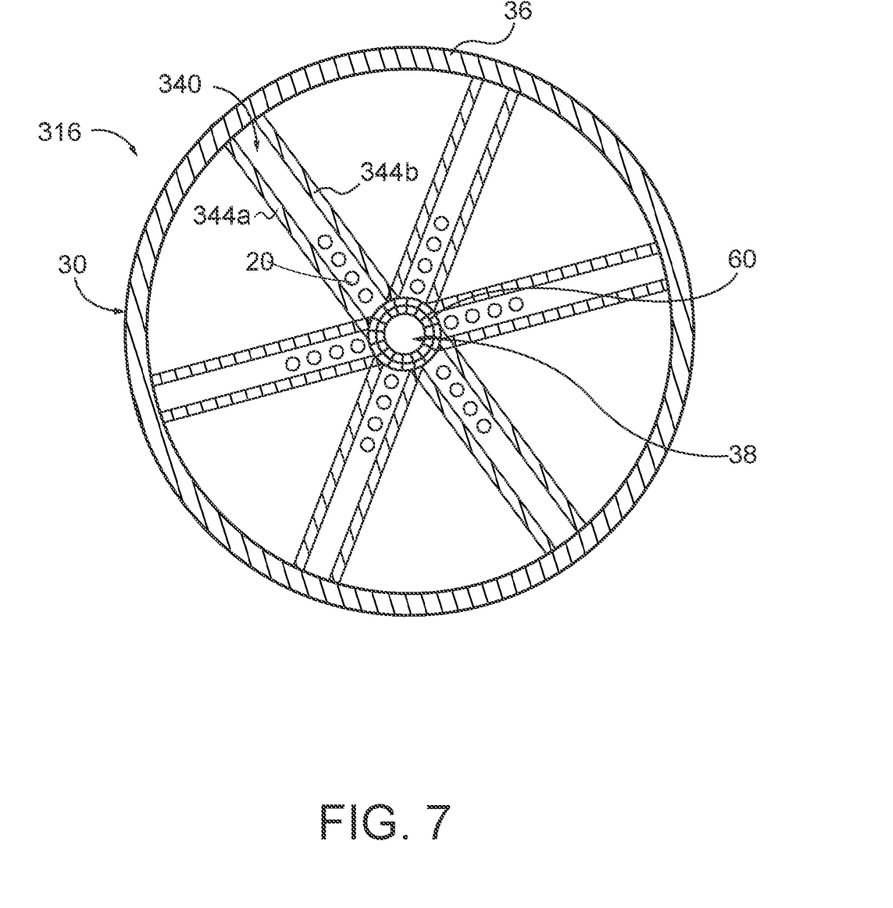
FIG. 7 is a top sectional view of the sensor array according to another embodiment of the disclosure.

Furthermore, as shown in FIG. 7, sensor array 316 has narrow partitions 340 that sized to conserve and/or reduce the amount of fluid needed to contact the sensors 20. In the embodiment shown in FIG. 7, the sensor array has first and second walls 344a and 344 that are near parallel to each other as the extend from the inlet 38 to the outer wall 36. In this manner, the walls 344a and 344b define a narrow flow path for fluid travel.

Referring back to FIGS. 2-4, each partition 40 has a port 42 into the fluid inlet 38. The sample of fluid F may be placed inside the fluid inlet 38 with any suitable device, such as a cartridge, syringe, pipette, or any device that can hold a fluid F. In one embodiment, the sample of fluid F is in an insert placed inside in the fluid control device 60 in the fluid inlet 38.

Each partition 40 includes at least one sensor 20. In the embodiment shown, one or more of the plurality of partitions 40 have a plurality of sensors 20a, 20b, 20c, . . . 20n. The reference number 20a, 20b, 20c, . . . 20n may be used interchangeably with reference number 20. In the illustrated embodiment, the sensor array 16 has eight different partitions 40, each having at least one sensor 20. Several of the partitions 40 shown in FIG. 2 include four sensors 20. Other partitions 40 include one sensor 20, two sensors 20, and three sensors 20. However, the number of sensors 20 per partition 40 can vary as needed. For example, the partitions 40 may include one sensor up to ten or more sensors. In cases where a partition 40 has multiple sensors 20, the sensors 20 may be different from each other and can test different analytes of interest. Alternatively, the sensors 20 in a particular partition may be similar to each other and test similar analytes. In addition, it should be appreciated the sensors 20 in each different partition may be different from each other. Likewise, several partitions 40 may include sensors that are similar and can test for the same analyte.

Each sensor(s) 20 is disposed along a path P aligned with the port 42. In this manner, fluid F placed in the fluid inlet 38 flows into one or more of the plurality of partitions 40 along the path P into contact with the sensor(s) 20. The first sensor 20a is spaced a first distance D1 from the fluid inlet 38. The first distance D1 may be consistent for each different partition 40. Subsequently arranged sensors 20b, 20c, etc., are spaced apart from each other a second distance D2 (i.e., an intra-sensor distance D2). The second distance D2 may be consistent for the sensors 20 in each different partition.

Each sensor 20 in the partitions 40 includes an electrically responsive component and a conductive elements, e.g., an electrode. The sensor 20 can be electronically coupled to the transducer 22 directly or indirectly via the conductive element. In operation, the sensor 20 generates a signal in response to contact with the fluid F. The transducer 22 forwards a signal to the computing device 14. The computing device 14 determines an analyte present in the fluid F based on the characteristics of the received signal from the sensor 20. Electrically responsive components of sensor(s) 20 are responsive to the fluid F upon contact with the fluid. Such fluid responsive sensors may be used to detect a variety of analytes of interest, such as blood gas analytes (e.g. pH, $pCO_2$, $pO_2$), electrolytes (Na+, K+, Ca++, Cl−), metabolites (Glucose, Lactate), CO-oximetry (tHb, HHb, $O_2$Hb, $sO_2$, COHb, MetHb), and/or neonatal total bilirubin. Other analytes may be detected based on sensor type.

Continuing with FIGS. 2-4, in one exemplary embodiment, the sensor array 16 includes a sensor assembly 50 that extends along the base 32 of the housing within each partition 40. The sensor assembly 50 includes one or more sensors 20 arranged along the path P. The sensors 20 in such a sensing assembly 50 may comprise sensing areas 52 that are open to an electrode (not shown) embedded in the sensor assembly 50. In one example, the sensor assembly 50 may include an upper substrate layer with through holes, a first intermediate layer with through holes, the electrode, a second intermediate layer below and adjacent to the electrode, and a lower substrate layer below and adjacent to the second intermediate layer. The different layers described above are not shown in FIGS. 2-4 for ease of illustration. The through holes in the upper planar layer and the intermediate layer are open to the electrode 54. The upper planar layer may include a flow channel that directs sample of fluid F to the sensor(s) 20 along the path P into the through holes and into contact with electrode. The electrode 54 is electrically coupled to the transducer 22 via traces 24 so that when the fluid F contacts the membrane on top of the electrode 54, the transducer 22 detects the signal response. The signal response is forwarded to the computing device 14 for analysis as described above. The sensing areas may be fully or partially filled with a chemical/reagent, which may react with fluid F to produce an analyte that can be detected by the electrode 54. For example, the sensing areas may be circular apertures, which extend through the upper substrate layer and the first intermediate layer. Alternatively, individual sensing areas may also be defined without the need for intermediate layers by applying chemicals and/or reagents directly to the electrode 54. The sensor assembly 50 as described above is similar to one sensor array in the opposed sensor arrays disclosed in International Patent Publication No. WO 2016011308, assigned to Siemens Health Care Diagnostics Inc. The sensors 20 and/or sensor assembly 50 describe above is not limiting. Any type of sensor 20 that detects an analyte or component of the fluid F may be used.

The sensor array 16 is designed so that a unique sensor 20 or combinations of sensors 20 may be utilized in different partitions 40. The flexibility in sensor selection and ability to use multiple partitions allows for a wide range analyte detection with a relatively lower sample volume, such as 100 µl or less. For instance, a low sample volume may be less than 100 µl, 80 µl, 60 µl, 40 µl, or 20 µl. The sample amount of fluid F, however, should be sufficient to travel far enough in the partition 40 to contact the number of sensors 20 (e.g. 1, 2, 3, 4, or more) that are present in the partition 40. In one example, the first distance D1 is similar for each partition 40. Thus, an evenly distributed sample of fluid F directed out of the fluid inlet 38 into each partition 40 will contact multiple sensors (in the illustrated embodiment). If those sensors are designed to detect different analytes, then a lower sample volume can be used to compile a substantially comprehensive panel of data on the sample of the fluid. Furthermore, in some cases as described above, similar sensors (i.e. sensors that detect the same analyte) are placed in different partitions. The use of similar sensors provides redundancy in case one sensor fails or returns a false positive.

Continuing with FIGS. 2-4, the sensor array 16 is configured to selectively direct the sample of fluid F received by the fluid inlet 38 into one or more of the plurality of partitions 40. As shown, a fluid control device 60 may be used to selectively open and close the ports 42, thereby controlling how fluid F enters the partitions 40. The fluid control device 60 allows for selective partitioning of the sample of fluid F into a single partition 40, a plurality of partitions 40, or every partition 40 in the sensor array 16. By controlling the flow of fluid into the partitions 40, the fluid control device 60 can control which tests are completed on the sample of fluid F. For instance, a first partition may include sensors 20 for detecting one type of analyte and a second partition may include sensors 20 for detecting a different analyte. The fluid control device 60 can direct the sample of fluid F to the first partition alone, to the second partition alone, or to both the first and second partitions. In this manner, the fluid control device 60 can maximize sample volume for the specific analytes of interest. The fluid control device 60 may include components (not shown), such as pumps, actuators, or other devices, that control the flow of fluid from the fluid inlet 38 into the partitions 40.

The fluid control device 60 can be implemented a number of different ways. In one example, the fluid control device 60 is a valve assembly (not shown) that is configured to open and close one or more of the ports 42. The valve assembly may be in electronic communication with the computing device 14. Control signals may cause the valve assembly to open one (up to all) of the ports 42 so that the sample of fluid F can flow into the different partitions 40. For instance, the computing device 14 may cause the valve to open a port 42 of one partition 40 and to close the port of a different partition 40.

In another example, the fluid control device 60 may include a plurality of membranes aligned with ports 42. The membranes may be configured to selectively rupture to permit fluid to pass through the ports 42 into the different partitions 40. For instance, the fluid control device 60 may include an insert that holds the sample of fluid F. The insert may be placed into the fluid inlet 38 in such a way to create a pressure differential between the fluid inlet 38 on one side of the membrane and the partition 40 on the other side of the membrane. The pressure differential causes the membrane to rupture thereby allowing fluid to enter the ports 42. In another example, the fluid control device 60 can be membrane that dissolves upon exposure to the fluid.

In another example, the fluid control device 60 is a cartridge that can be inserted in the fluid inlet 38. The cartridge may include a chamber that holds the sample of fluid F and a plurality of outlets that open to the chamber. The cartridge can be placed in the fluid inlet 38 so that cartridge outlets align with the ports 42 of the partitions 40. In one example, the cartridge has a first position whereby the cartridge blocks the ports 42 of each partition. The cartridge may be rotated into a second position so that cartridge outlets align with the ports 42 to deliver the fluid from the cartridge into one or more of the plurality of partitions.

In another embodiment, each partition can be a designed as a single use partition. As such, each respective partition can be sealed so as to prevent cross-contamination during use. For instance, the sensor array may include partitions that are individually sealed. One means to accomplish is with monolithic partitions that can be positioned in the housing around the inlet. The monolithic partitions can interface with the inlet to allow selective flow into the partition. A fluid control device can be configured to open the port to one partition to cause fluid to flow into that single partition. In this way, only one partition is used at a time. The sensor array can be used multiple times for subsequent tests.

The inventive concepts are not limited in their application to the details of construction and the arrangement of the components set forth in the description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

Numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a nonexclusive inclusion. For example, a composition, a process, method, article, or apparatus that comprises a list of elements is not necessarily limited to only those elements but may include other elements not expressly listed or inherently present therein.

As used herein the terms "approximately," "about," "substantially" and variations thereof are intended to include not only the exact value qualified by the term, but to also include some slight deviations therefrom, such as deviations caused by measuring error, manufacturing tolerances, wear and tear on components or structures, stress exerted on structures, and combinations thereof, for example.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present). An inclusive or may be understood as being the equivalent to: at least one of condition A or B.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The invention claimed is:

1. A sensor array for analyzing a fluid, the sensor array comprising:
    a housing having a base, a top spaced above the base, and an outer wall that extends from the base to the top;
    a single central fluid inlet in the housing that is sized to receive a sample of the fluid;
    a plurality of partitions disposed adjacently around the fluid inlet and substantially isolated from each other, each partition having a port disposed at the fluid inlet for receiving a portion of the sample of fluid received by the fluid inlet; and at least one sensor in each partition,
    wherein the at least one sensor is responsive to the fluid when the fluid contacts the at least one sensor within each partition, wherein the sensor array is configured to selectively direct the sample of fluid received by the one or more of the plurality of partitions from the fluid inlet into contact with the at least one sensor.

2. The sensor array of claim 1, wherein the at least one sensor is spaced from the port along a linear path in order to minimize a distance of travel of the fluid from the fluid inlet to the at least one sensor.

3. The sensor array of claim 1, wherein the plurality of partitions is a first partition and a second partition, wherein the first partition includes a plurality of first sensors and the second partition includes a plurality of second sensors.

4. The sensor array of claim 1, wherein each partition has a plurality of sensors that are similar to each other.

5. The sensor array of claim 1, wherein each partition has a plurality of sensors that are different from each other.

6. The sensor array of claim 1, wherein the at least one sensor among the plurality of partitions is different from each other.

7. The sensor array of claim 1, wherein the plurality of partitions is a first partition and a second partition, wherein the first partition has a first volume and the second partition has second volume that is greater than the first volume.

8. The sensor array of claim 1, further comprising at least one interior wall that extends from the fluid inlet to the outer wall so as to define the plurality of partitions.

9. The sensor array of claim 8, wherein the at least one interior wall is a plurality of separate walls that extend from the fluid inlet to the outer wall.

10. The sensor array of claim 1, further comprising a fluid control device for selectively opening and closing the port of each partition.

11. The sensor array of claim 10, wherein the fluid control device is a valve assembly for selectively opening and closing the port of each partition.

12. The sensor array of claim 10, wherein the fluid control device includes a plurality of membranes aligned with each port, wherein each membrane is configured to selectively rupture to permit the fluid to pass from the fluid inlet through the port into the respective partition.

13. The sensor array of claim 10, wherein the fluid control device includes a cartridge that is configured to be inserted into the fluid inlet, wherein the cartridge has one or more outlets that are configured to align with one or more of the ports of the plurality of partitions so as to permit the sample of fluid to enter the one or more of the plurality of partitions.

14. The sensor array of claim 1, further comprising a dispensing device that includes an arm adapted to deliver the sample of fluid to the fluid inlet, wherein either the housing or the arm are moveable so as to deliver the sample of fluid to the fluid inlet.

15. The sensor array of claim 1, further comprising at least one transducer, wherein each sensor includes an electrically responsive material and a trace coupled to the electrically responsive material and the at least one transducer.

16. A system, comprising:
    a sample analyzer for analyzing a sample of fluid, the sample analyzer including:
    a) the sensor array of claim 1; and
    b) a computing device in electronic communication with the sensor array.

17. The system of claim 16, wherein the at least one sensor generates a signal in response to contact with the fluid, wherein the computing device is configured determine an analyte present in the fluid based on the signal.

18. The system of claim 16, wherein the computing device is configured to control partitioning of the sample of fluid from the fluid inlet into the one or more of the plurality of partitions.

19. A sample analyzer for analyzing a sample of fluid, the sample analyzer comprising:
    a sensor array according to claim 1; and
    a computing device in electronic communication with sensor array, wherein the computing device is configured to selectively direct the sample of fluid received by the fluid inlet into one or more of the plurality of partitions.

20. The sample analyzer of claim 19, wherein the at least one sensor generates a signal in response to contact with the fluid, wherein the computing device analyzes the fluid based on the signal.

* * * * *